(12) United States Patent
Duncton et al.

(10) Patent No.: US 8,754,251 B2
(45) Date of Patent: Jun. 17, 2014

(54) CYCLOPROPYL PIDA BORONATE

(71) Applicant: Rigel Pharmaceuticals, Inc., South San Francisco, CA (US)

(72) Inventors: Matthew Duncton, San Bruno, CA (US); Martin D. Burke, Urbana, IL (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 13/912,000

(22) Filed: Jun. 6, 2013

(65) Prior Publication Data

US 2013/0331585 A1  Dec. 12, 2013

Related U.S. Application Data

(60) Provisional application No. 61/656,293, filed on Jun. 6, 2012.

(51) Int. Cl.
*C07F 5/02* (2006.01)
*C07J 1/00* (2006.01)
*C07C 19/08* (2006.01)

(52) U.S. Cl.
USPC ............................... 558/289; 568/6; 544/105

(58) Field of Classification Search
USPC ............................... 558/289; 568/6; 544/105
See application file for complete search history.

(56) References Cited

U.S. PATENT DOCUMENTS

| 2009/0030238 A1 | 1/2009 | Burke et al. |
| 2010/0121062 A1 | 5/2010 | Burke et al. |
| 2011/0130415 A1 | 6/2011 | Singh et al. |

FOREIGN PATENT DOCUMENTS

| WO | 2009014550 | 1/2009 |
| WO | 2010104818 | 9/2010 |
| WO | 2012075316 | 6/2012 |

OTHER PUBLICATIONS

Gillis et al. Journal of the American Chemical Society (2007), 129(21), 6716-6717.*
Brak & Ellman (2010) "Asymmetric Rh(I)-catalyzed addition of MIDA boronates to N-tert-butanesulfinyl aldimines: development and comparison to trifluoroborates" J Org Chem, 75(9):3147-3150.
Duncton et al. (2010) "Dibutyl 2-(trifluoromethyl)cyclopropylboronate as a useful (trifluoromethyl)-cyclopropyl donor: application to antagonists of TRPV1" Tetrahedron Letters 51:1009-1011.
Gillis & Burke (2007) "A Simple and Modular Strategy for Small Molecule Synthesis: Iterative Suzuki-Miyaura Coupling of B-Protected Haloboronic Acid Building Blocks" J Am Chem Soc, 129:6716-6717.
Gillman & Jones (1943) "2,2,2-Trifluoroethylamine and 2,2,2-Trifluorodiazoethane" J Am Chem Soc, 65:1458-1460.
Li & Burke (2011) "Pinene-Derived Iminodiacetic Acid (PIDA): A Powerful Ligand for Stereoselective Synthesis and Iterative Cross-Coupling of C(sp3) Boronate Building Blocks" J Am Chem Soc, 133:13774-13777.
Miyaura & Suzuki (1995) "Palladium-Catalyzed Cross-Coupling Reactions of Organoboron Compounds" Chem Rev, 95:2457-2483.
Qin et al. (2002) "Well-Defined Boron-Containing Polymeric Lewis Acids" J Am Chem.Soc, 124:12672-12673.
Qin et al. (2004) "A New Route to Organoboron Polymers via Highly Selective Polymer Modification Reactions" Macromolecules, 37:7123-7131.
Suzuki (1999) "Recent advances in the cross-coupling reactions of organoboron derivatives with organic electrophiles, 1995-1998" J Organomet Chem, 576:147-168.
Tang et al. (2010) "Silver-Catalyzed Late-Stage Fluorination" J Am Chem Soc, 132:12150-12154.
Wallace & Chen (2002) "Cyclopropylboronic acid: synthesis and Suzuki cross-coupling reactions" Tetrahedron Letters 32:6987-6990.
Wolfe et al. (1999) "Highly Active Palladium Catalysts for Suzuki Coupling Reactions" J Am Chem Soc, 121:9550-9561.

* cited by examiner

*Primary Examiner* — Kahsay Habte
(74) *Attorney, Agent, or Firm* — Carol L. Francis; Rudy J. Ng; Travis Young

(57) ABSTRACT

Provided are protected cyclopropylboronic acids that include a substituted cyclopropyl group and a boronic ester group having a protecting group. The protecting group is a pinene-derived iminodiacetic acid (PIDA) group or PIDA-based group.

56 Claims, No Drawings

CYCLOPROPYL PIDA BORONATE

The cyclopropyl group is a popular motif for exploring structure-activity relationships in medicinal chemistry. However, substituted cyclopropyl groups have been less frequently employed, in part due to their more complicated installation. Certain methods to introduce cyclopropyl groups can be found in Tetrahedron Letters 51 (2010) 1009-1011. However, there are still a limited number of methods to prepare such compounds, particularly with stereocontrol.

SUMMARY

This disclosure concerns a protected cyclopropylboronic acid that includes a substituted cyclopropyl group and a boronic ester group having a protecting group. The protecting group is pinene-derived iminodiacetic acid (PIDA) group or PIDA-based group.

The protected cyclopropylboronic acid can undergo deprotection under mild conditions with high yields. Such a system can control the reactivity of boronic acids and expand the versatility of organoboronic acids in transition metal catalyzed reactions, such as palladium catalyzed cross-coupling reactions, for example, the Suzuki reaction or of other reactions of boronic acids. Thus, the protected cyclopropylboronic acid can deliver a substituted cyclopropyl group in a coupling reaction with improved selectivity compared to a corresponding reaction without use of the protected cyclopropylboronic acid.

One embodiment provides a protected organoboronic acid of the formula I:

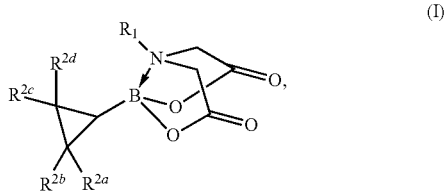

(I)

wherein
$R^1$ is selected from cycloalkyl and substituted cycloalkyl; and
$R^{2a}$, $R^{2b}$, $R^{2c}$, and $R^{2d}$ are independently selected from hydrogen, alkyl, substituted alkyl, halogen, hydroxyl, cyano, phosphate, alkoxy, substituted alkoxy, carboxyl, carboxyl ester, aryl, substituted aryl, heteroaryl, substituted heteroaryl, heterocyclyl, substituted heterocyclyl, alkenyl, substituted alkenyl, amino, substituted amino, acyl, acylamino, aminoacyl, alkoxycarbonylamino, thiol, alkylthio, substituted thioalkoxy, and sulfonyl,
wherein at least one of $R^{2a}$, $R^{2b}$, $R^{2c}$, and $R^{2d}$ is not hydrogen.

Also provided are methods of preparing the protected cyclopropylboronic acids and method of using the protected cyclopropylboronic acids in chemical reactions. Further provided are methods and reagents for installation of a substituted cyclopropyl group with stereochemical control.

DETAILED DESCRIPTION

This disclosure concerns a protected cyclopropylboronic acid that includes a substituted cyclopropyl group and a boronic ester group having a PIDA or PIDA-based protecting group.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range, is specifically contemplated. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978.

The nomenclature used herein to name the subject compounds is illustrated in the Examples herein. This nomenclature has generally been derived using the commercially-available AutoNom software (MDL, San Leandro, Calif.).

Terms

The following terms have the following meanings unless otherwise indicated. Any undefined terms have their art recognized meanings.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —$SO_2$-alkyl, —$SO_2$-aryl, —$SO_2$-heteroaryl, and —$NR^aR^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —$NR^{10}$—, —$NR^{10}C(O)$—, —$C(O)NR^{10}$— and the like. This term includes, by way of example, methylene (—$CH_2$—), ethylene (—$CH_2CH_2$—), n-propylene (—$CH_2CH_2CH_2$—), iso-propylene (—$CH_2CH(CH_3)$—), (—$C(CH_3)_2CH_2CH_2$—), (—$C(CH_3)_2CH_2C(O)$—), (—$C(CH_3)_2CH_2C(O)NH$—), (—$CH(CH_3)CH_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—$CH_2C$≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl, and —$SO_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group $CH_3C(O)$—

"Acylamino" refers to the groups —$NR^{20}C(O)$alkyl, —$NR^{20}C(O)$substituted alkyl, N $R^{20}C(O)$cycloalkyl, —$NR^{20}C(O)$substituted cycloalkyl, —$NR^{20}C(O)$cycloalkenyl, —$NR^{20}C(O)$substituted cycloalkenyl, —$NR^{20}C(O)$alkenyl, —$NR^{20}C(O)$substituted alkenyl, —$NR^{20}C(O)$alkynyl, —$NR^{20}C(O)$substituted alkynyl, —$NR^{20}C(O)$aryl, —$NR^{20}C(O)$substituted aryl, —$NR^{20}C(O)$heteroaryl, —$NR^{20}C(O)$substituted heteroaryl, —$NR^{20}C(O)$heterocyclic, and —$NR^{20}C(O)$substituted heterocyclic, wherein $R^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —$C(O)NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —$SO_2NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where $R^{21}$ and $R^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —$NR^{21}SO_2R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic, provided that the point of attachment is through an atom of the aromatic aryl group. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —$NH_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —$N_3$.

The term "hydrazino" refers to $R^1R^2N$—$NR^3R^4$ wherein $R^1$, $R^2$, $R^3$, and $R^4$ are each independently hydrogen, alkyl, aryl, heteroaryl, or acyl.

"Carboxyl," "carboxy" or "carboxylate" refers to —$CO_2H$ or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Examples of substituted cycloalkyl groups include, but are not limited to, isopinocampheyl, and the like.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen, and sulfur within the ring. Such heteroaryl groups can have a single ring (e.g., pyridinyl, imidazolyl or furyl) or multiple condensed rings (e.g., indolizinyl, quinolinyl, benzimidazolyl or benzothienyl), wherein the condensed rings may or may not be aromatic and/or contain a heteroatom, provided that the point of attachment is through an atom of the aromatic heteroaryl group. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 15 ring atoms, including 1 to 4 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cylcoalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cylcoalkyl, OSO$_2$-cycloalkenyl, OSO$_2$-substituted cylcoalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^{30}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means e.g. that one of the counter ions for such divalent alkali earth ions can be an ionized form of a compound of the invention and the other a typical counter ion such as chloride, or two ionized compounds of the invention can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the groups disclosed with respect to the individual terms herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$, M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3^-$M$^+$, —SO$_3$R$^{70}$, —OSO$_2$R$^{70}$, —OSO$_3^-$M$^+$, —OSO$_3$R$^{70}$, —PO$_3^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the disclosure herein, substituent groups for hydrogens on nitrogen atoms in "substituted" heteroalkyl and cycloheteroalkyl groups are, unless otherwise specified, —R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C (S)R⁷, —NR⁷⁰C(O)OR⁷⁰, —NR⁷⁰C(S)OR⁷⁰, —NR⁷⁰C(O) NR⁸⁰R⁸⁰, —NR⁷⁰C(NR⁷⁰)R⁷⁰ and —NR⁷⁰C(NR⁷⁰) NR⁸⁰R⁸⁰, where R⁶⁰, R⁷⁰, R⁸⁰ and M⁺ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically nonfeasible. In addition, the subject compounds include all stereochemical isomers arising from the substitution of these compounds.

The term "salt thereof" means a compound formed when the hydrogen of an acid is replaced by a cation, such as a metal cation or an organic cation and the like. Where applicable, the salt is a pharmaceutically acceptable salt, although this is not required for salts of compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

Representative Embodiments

The following substituents and values are intended to provide representative examples of various aspects and embodiments. These representative values are intended to further define and illustrate such aspects and embodiments and are not intended to exclude other embodiments or to limit the scope of this invention. In this regard, the representation that a particular value or substituent is preferred is not intended in any way to exclude other values or substituents from this invention unless specifically indicated.

These compounds may contain one or more chiral centers and therefore, the embodiments are directed to racemic mixtures; pure stereoisomers (i.e., enantiomers or diastereomers); stereoisomer-enriched mixtures and the like unless otherwise indicated. When a particular stereoisomer is shown or named herein, it will be understood by those skilled in the art that minor amounts of other stereoisomers may be present in the compositions unless otherwise indicated, provided that the desired utility of the composition as a whole is not eliminated by the presence of such other isomers.

The compounds described also include isotopically labeled compounds where one or more atoms have an atomic mass different from the atomic mass conventionally found in nature. Examples of isotopes that may be incorporated into the compounds disclosed herein include, but are not limited to, ²H, ³H, ¹¹C, ¹³C, ¹⁴C, ¹⁵N, ¹⁸O, ¹⁷O, etc. Thus, the disclosed compounds may be enriched in one or more of these isotopes relative to the natural abundance of such isotope. By way of example, deuterium (²H) has a natural abundance of about 0.015%. Accordingly, for approximately every 6,500 hydrogen atoms occurring in nature, there is one deuterium atom. Specifically contemplated herein are compounds enriched in deuterium at one or more positions. Thus, deuterium containing compounds of the disclosure have deuterium at one or more positions (as the case may be) in an abundance of greater than 0.015%.

Protected Cyclopropylboronic Acids

This disclosure concerns a protected cyclopropylboronic acid that includes a substituted cyclopropyl group and a boronic ester group having a protecting group. The protecting group is a pinene-derived iminodiacetic acid (PIDA) group or PIDA-based group.

The protected cyclopropylboronic acid can undergo deprotection under mild conditions with high yields. Such a system can control the reactivity of boronic acids and expand the versatility of the Suzuki reaction or of other reactions of boronic acids. Thus, the protected cyclopropylboronic acid can deliver a substituted cyclopropyl group in a coupling reaction with improved selectivity compared to a corresponding reaction without use of the protected cyclopropylboronic acid.

A cyclopropylboronic acid has a general structure:

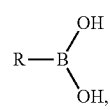

wherein R is a cyclopropyl group that is bonded to the boron through a boron-carbon bond, wherein the cyclopropyl group has at least one substituent.

A protected cyclopropylboronic acid is a chemical transform of a cyclopropylboronic acid, in which the boron has a lower chemical reactivity relative to the original cyclopropylboronic acid. A protected cyclopropylboronic acid has a general structure:

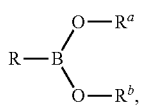

wherein $R^a$ and $R^b$ are independently hydrogen or an organic group, as defined herein and examples of which are alkyl, acyl, cycloalkyl, aryl and the like;

wherein at least one of $R^a$ and $R^b$ is not hydrogen; and

R is a cyclopropyl group that is bonded to the boron through a boron-carbon bond, wherein the cyclopropyl group has at least one substituent.

A protected cyclopropylboronic acid can also be referred to as a cyclopropylboronate or cyclopropylboronic ester.

This disclosure concerns a protected cyclopropylboronic acid that includes a substituted cyclopropyl group and a boronic ester group having a PIDA or PIDA-based protecting group, as shown in the formulae below:

Formula I

One embodiment provides a protected organoboronic acid of the formula I:

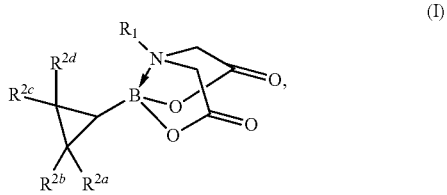

wherein $R^1$ is selected from cycloalkyl and substituted cycloalkyl; and $R^{2a}$, $R^{2b}$, $R^{2c}$, and $R^{2d}$ are independently selected from hydrogen, alkyl, substituted alkyl, halogen, hydroxyl, cyano, phosphate, alkoxy, substituted alkoxy, carboxyl, carboxyl ester, aryl, substituted aryl, heteroaryl, substituted heteroaryl, heterocyclyl, substituted heterocyclyl, alkenyl, substituted alkenyl, amino, substituted amino, acyl, acylamino, aminoacyl, alkoxycarbonylamino, thiol, alkylthio, substituted thioalkoxy, and sulfonyl, wherein at least one of $R^{2a}$, $R^{2b}$, $R^{2c}$, and $R^{2d}$ is not hydrogen.

In formula I, $R^1$ is selected from cycloalkyl and substituted cycloalkyl. In certain embodiments, $R^1$ is cycloalkyl. In certain embodiments, $R^1$ is substituted cycloalkyl. In certain embodiments, $R^1$ is a homochiral moiety. By way of illustration, examples of such homochiral $R^1$ moieties include isopinocampheyl in the R and the S configurations.

In formula I, $R^{2a}$, $R^{2b}$, $R^{2c}$, and $R^{2d}$ are independently selected from hydrogen, alkyl, substituted alkyl, halogen, hydroxyl, cyano, phosphate, alkoxy, substituted alkoxy, carboxyl, carboxyl ester, aryl, substituted aryl, heteroaryl, substituted heteroaryl, heterocyclyl, substituted heterocyclyl, alkenyl, substituted alkenyl, amino, substituted amino, acyl, acylamino, aminoacyl, alkoxycarbonylamino, thiol, alkylthio, substituted thioalkoxy, and sulfonyl, wherein at least one of $R^{2a}$, $R^{2b}$, $R^{2c}$, and $R^{2d}$ is not hydrogen.

In certain embodiments, at least one of $R^{2a}$, $R^{2b}$, $R^{2c}$, and $R^{2d}$ is alkyl or substituted alkyl and the others are hydrogen. In certain embodiments, one of $R^{2a}$, $R^{2b}$, $R^{2c}$, and $R^{2d}$ is alkyl or substituted alkyl and the others are hydrogen.

In certain embodiments, at least one of $R^{2a}$, $R^{2b}$, $R^{2c}$, and $R^{2d}$ is substituted alkyl and the others are hydrogen. In certain embodiments, one of $R^{2a}$, $R^{2b}$, $R^{2c}$, and $R^{2d}$ is substituted alkyl and the others are hydrogen. In certain embodiments, at least one of $R^{2a}$, $R^{2b}$, $R^{2c}$, and $R^{2d}$ is trifluoromethyl and the others are hydrogen. In certain embodiments, one of $R^{2a}$, $R^{2b}$, $R^{2c}$, and $R^{2d}$ is trifluoromethyl and the others are hydrogen. In certain embodiments, at least one of $R^{2a}$, $R^{2b}$, $R^{2c}$, and $R^{2d}$ is alkyl and the others are hydrogen. In certain embodiments, one of $R^{2a}$, $R^{2b}$, $R^{2c}$, and $R^{2d}$ is alkyl and the others are hydrogen.

In certain embodiments, at least one of $R^{2a}$, $R^{2b}$, $R^{2c}$, and $R^{2d}$ is halogen, hydroxyl, cyano, or phosphate, and the others are hydrogen. In certain embodiments, at least one of $R^{2a}$, $R^{2b}$, $R^{2c}$, and $R^{2d}$ is alkoxy or substituted alkoxy, and the others are hydrogen. In certain embodiments, at least one of $R^{2a}$, $R^{2b}$, $R^{2c}$, and $R^{2d}$ is carboxyl or carboxyl ester, and the others are hydrogen. In certain embodiments, at least one of $R^{2a}$, $R^{2b}$, $R^{2c}$, and $R^{2d}$ is aryl or substituted aryl, and the others are hydrogen. In certain embodiments, at least one of $R^{2a}$, $R^{2b}$, $R^{2c}$, and $R^{2d}$ is heteroaryl, substituted heteroaryl, heterocyclyl, or substituted heterocyclyl, and the others are hydrogen. In certain embodiments, at least one of $R^{2a}$, $R^{2b}$, $R^{2c}$, and $R^{2d}$ is alkenyl or substituted alkenyl, and the others are hydrogen. In certain embodiments, at least one of $R^{2a}$, $R^{2b}$, $R^{2c}$, and $R^{2d}$ is amino or substituted amino, and the others are hydrogen. In certain embodiments, at least one of $R^{2a}$, $R^{2b}$, $R^{2c}$, and $R^{2d}$ is acyl, acylamino, aminoacyl, or alkoxycarbonylamino, and the others are hydrogen. In certain embodiments, at least one of $R^{2a}$, $R^{2b}$, $R^{2c}$, and $R^{2d}$ is thiol, alkylthio, substituted thioalkoxy, and sulfonyl and the others are hydrogen.

Formula II

One embodiment provides a protected organoboronic acid of the formula II:

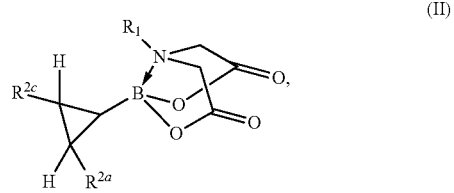

wherein $R^1$ is selected from cycloalkyl and substituted cycloalkyl; and $R^{2a}$ and $R^{2c}$ are independently selected from alkyl, substituted alkyl, halogen, hydroxyl, cyano, phosphate, alkoxy, substituted alkoxy, carboxyl, carboxyl ester, aryl, substituted aryl, heteroaryl, substituted heteroaryl, heterocyclyl, substituted heterocyclyl, alkenyl, substituted alkenyl, amino, substituted amino, acyl, acylamino, aminoacyl, alkoxycarbonylamino, thiol, alkylthio, substituted thioalkoxy, and sulfonyl.

In formula II, $R^1$ is selected from cycloalkyl and substituted cycloalkyl. In certain embodiments, $R^1$ is cycloalkyl. In certain embodiments, $R^1$ is substituted cycloalkyl. In certain embodiments, $R^1$ is isopinocampheyl.

In formula II, $R^{2a}$ is selected from alkyl, substituted alkyl, haloalkyl, halogen, hydroxyl, cyano, phosphate, alkoxy, substituted alkoxy, carboxyl, carboxyl ester, aryl, substituted aryl, heteroaryl, substituted heteroaryl, heterocyclyl, substituted heterocyclyl, alkenyl, substituted alkenyl, amino, substituted amino, acyl, acylamino, aminoacyl, alkoxycarbonylamino, thiol, alkylthio, substituted thioalkoxy, and sulfonyl.

In certain embodiments, $R^{2a}$ is alkyl or substituted alkyl. In certain embodiments, $R^{2a}$ is substituted alkyl. In certain embodiments, $R^{2a}$ is trifluoromethyl. In certain embodiments, $R^{2a}$ is alkyl.

In certain embodiments, $R^{2a}$ is halogen, hydroxyl, cyano, or phosphate. In certain embodiments, $R^{2a}$ is alkoxy or substituted alkoxy. In certain embodiments, $R^{2a}$ is carboxyl or carboxyl ester. In certain embodiments, $R^{2a}$ is aryl or substituted aryl. In certain embodiments, $R^{2a}$ is heteroaryl, substituted heteroaryl, heterocyclyl, or substituted heterocyclyl. In certain embodiments, $R^{2a}$ is alkenyl or substituted alkenyl. In certain embodiments, $R^{2a}$ is amino or substituted amino. In certain embodiments, $R^{2a}$ is acyl, acylamino, aminoacyl, or alkoxycarbonylamino. In certain embodiments, $R^{2a}$ is thiol, alkylthiol, substituted thioalkoxy, and sulfonyl.

In formula II, $R^{2c}$ is selected from alkyl, substituted alkyl, haloalkyl, halogen, hydroxyl, cyano, phosphate, alkoxy, substituted alkoxy, carboxyl, carboxyl ester, aryl, substituted aryl, heteroaryl, substituted heteroaryl, heterocyclyl, substituted heterocyclyl, alkenyl, substituted alkenyl, amino, substituted amino, acyl, acylamino, aminoacyl, alkoxycarbonylamino, thiol, alkylthiol, substituted thioalkoxy, and sulfonyl.

In certain embodiments, $R^{2c}$ is alkyl or substituted alkyl. In certain embodiments, $R^{2c}$ is substituted alkyl. In certain embodiments, $R^{2a}$ is trifluoromethyl. In certain embodiments, $R^{2c}$ is alkyl.

In certain embodiments, $R^{2c}$ is halogen, hydroxyl, cyano, or phosphate. In certain embodiments, $R^{2c}$ is alkoxy or substituted alkoxy. In certain embodiments, $R^{2c}$ is carboxyl or carboxyl ester. In certain embodiments, $R^{2c}$ is aryl or substituted aryl. In certain embodiments, $R^{2c}$ is heteroaryl, substituted heteroaryl, heterocyclyl, or substituted heterocyclyl. In certain embodiments, $R^{2c}$ is alkenyl or substituted alkenyl. In certain embodiments, $R^{2c}$ is amino or substituted amino. In certain embodiments, $R^{2c}$ is acyl, acylamino, aminoacyl, or alkoxycarbonylamino. In certain embodiments, $R^{2c}$ is thiol, alkylthiol, substituted thioalkoxy, and sulfonyl.

In certain embodiments, the protected organoboronic acid of the formula II has a trans stereochemistry with respect to the cyclopropyl ring. For example, the trans isomer of the protected organoboronic acid of formula II has the structure, shown below:

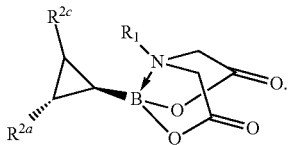

A composition can include a mixture of diastereomers, or a racemic mixture of a single diastereomer of the protected organoboronic acid above. Alternatively, such racemic mixtures can be resolved by techniques known to those of skill in the art of organic synthesis, or compounds of the formula above can be prepared in optically active form as is known to those of skill in the art.

In certain embodiments, the protected organoboronic acid of the formula II has a trans stereochemistry with respect to one or more substituents on the cyclopropyl ring. The protected organoboronic acid may also have a cis relationship with one or more substituents on the cyclopropyl ring of formula II. An example of such a structure having both a cis and a trans substituent relative to the protected organoboronic acid is illustrated by the structure, shown below:

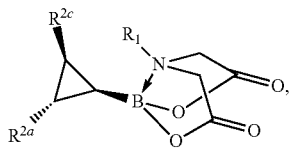

wherein $R^{2a}$ and $R^{2c}$ are trans and cis, respectively, relative to the boron substituent. A composition can include a racemic mixture of stereoisomers of the protected organoboronic acid of the formula above. Alternatively, compounds of the formula above can be prepared in optically active form or can be resolved to provide an optically active compound.

In certain embodiments, the protected organoboronic acid of the formula II is trans with respect to one or more substituents on the cyclopropyl ring. One example of such a protected organoboronic acid of formula II is illustrated by the structure shown below:

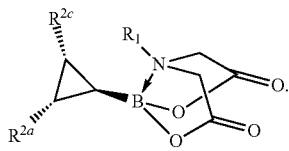

wherein, $R^{2a}$ and $R^{2c}$ are trans relative to the boron substituent. A composition can include a racemic mixture of a single diastereomer of the protected organoboronic acid of formula II.

Formula III

One embodiment provides a protected organoboronic acid of the formula III:

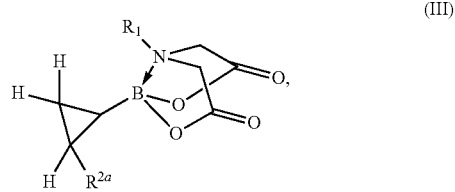

(III)

wherein $R^1$ is selected from cycloalkyl and substituted cycloalkyl; and $R^{2a}$ is selected from alkyl, substituted alkyl, halogen, hydroxyl, cyano, phosphate, alkoxy, substituted alkoxy, carboxyl, carboxyl ester, aryl, substituted aryl, heteroaryl, substituted heteroaryl, heterocyclyl, substituted heterocyclyl, alkenyl, substituted alkenyl, amino, substituted amino, acyl, acylamino, aminoacyl, alkoxycarbonylamino, thiol, alkylthiol, substituted thioalkoxy, and sulfonyl.

In formula III, $R^1$ is selected from cycloalkyl and substituted cycloalkyl. In certain embodiments, $R^1$ is cycloalkyl. In certain embodiments, $R^1$ is substituted cycloalkyl. In certain embodiments, $R^1$ is isopinocampheyl.

In formula III, $R^{2a}$ is selected from alkyl, substituted alkyl, haloalkyl, halogen, hydroxyl, cyano, phosphate, alkoxy, substituted alkoxy, carboxyl, carboxyl ester, aryl, substituted aryl, heteroaryl, substituted heteroaryl, heterocyclyl, substituted heterocyclyl, alkenyl, substituted alkenyl, amino, substituted amino, acyl, acylamino, aminoacyl, alkoxycarbonylamino, thiol, alkylthiol, substituted thioalkoxy, and sulfonyl.

In certain embodiments, $R^{2a}$ is alkyl or substituted alkyl. In certain embodiments, $R^{2a}$ is substituted alkyl. In certain embodiments, $R^{2a}$ is trifluoromethyl. In certain embodiments, $R^{2a}$ is alkyl.

In certain embodiments, $R^{2a}$ is halogen, hydroxyl, cyano, or phosphate. In certain embodiments, $R^{2a}$ is alkoxy or substituted alkoxy. In certain embodiments, $R^{2a}$ is carboxyl or carboxyl ester. In certain embodiments, $R^{2a}$ is aryl or substituted aryl. In certain embodiments, $R^{2a}$ is heteroaryl, substituted heteroaryl, heterocyclyl, or substituted heterocyclyl. In certain embodiments, $R^{2a}$ is alkenyl or substituted alkenyl. In certain embodiments, $R^{2a}$ is amino or substituted amino. In certain embodiments, $R^{2a}$ is acyl, acylamino, aminoacyl, or alkoxycarbonylamino. In certain embodiments, $R^{2a}$ is thiol, alkylthiol, substituted thioalkoxy, and sulfonyl.

In certain embodiments of the protected organoboronic acid of the formula II, $R^{2a}$ and the boron substituent of the cyclopropyl ring have a trans relative stereochemistry. For example, the protected organoboronic acid of the formula III may have a structure, shown below:

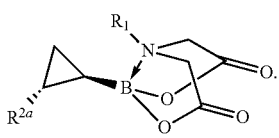

A composition can include racemic mixture of trans stereoisomers of the protected organoboronic acid of the formula III.

Formula IV

One embodiment provides a protected organoboronic acid of the formula IV:

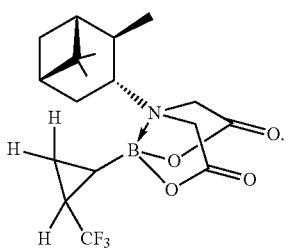

In certain embodiments, the protected organoboronic acid of the formula IV has a trans stereochemistry with respect to the cyclopropyl ring. Such trans relative stereochemistry is illustrated in the structure below:

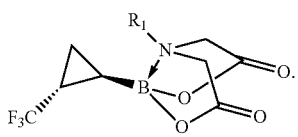

A composition can include a racemic mixture of trans stereoisomers of the protected organoboronic acid of the formula IV. When $R_1$ is a homochiral moiety, the composition above includes two trans diastereomers. Alternatively, such racemic mixtures can be partially or completely resolved or compounds of the formula above can be prepared enantioselectively to provide optically active compositions, or when $R_1$ is a homochiral moiety, such compounds can be prepared diastereoselectively or separated to provide single, optically active stereoisomers.

Formula V

One embodiment provides a protected organoboronic acid of the formula V:

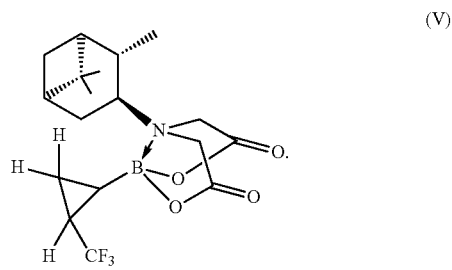

In certain embodiments, the protected organoboronic acid of the formula V has a trans stereochemistry with respect to the cyclopropyl ring. Such trans relative stereochemistry is illustrated in the structure below:

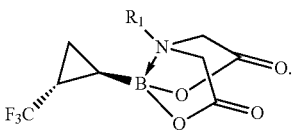

A composition can include a racemic mixture of trans stereoisomers of the protected organoboronic acid of the formula V. Alternatively, such racemic mixtures can be resolved or compounds of the formula above can be prepared enantioselectively to provide optically active compositions.

Stereochemistry of Protected Cyclopropylboronic Acids

In certain embodiments of formulae I-III, $R^1$ is a substituted cycloalkyl, such as isopinocampheyl. The isopinocampheyl group may be derived from (+)-alpha-pinene or (−)-alpha-pinene. For example, the isopinocampheyl group of the protected cyclopropylboronic acids may have stereochemistry as shown in formula IV above. In other instances, the protected cyclopropylboronic acid may have an isopinocampheyl group with stereochemistry as shown in formula V above.

Additional aspects of protected cyclopropylboronic acids are disclosed in U.S. application Ser. No. 13/309,400, filed Dec. 1, 2011, the disclosure of which is incorporated herein by reference in its entirety.

Synthesis of Compounds

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4$^{th}$ edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds can be synthesized via a variety of different synthetic routes using commercially available starting materials and/or starting materials prepared by conventional synthetic methods. Suitable exemplary methods that can be adapted to synthesize the protected cyclopropylboronic acid compounds are found in U.S. Patent Publication Nos. 2009/0030238 and 2010/0121062, the disclosures of each of which are incorporated herein by reference in their entireties.

Exemplary synthetic methods for the protected cyclopropylboronic acid compounds described herein are described below.

Synthesis of Protected Cyclopropylboronic Acids

Protected cyclopropylboronic acids according to formula (1c) can be prepared by cyclopropanation reaction of the corresponding PIDA or PIDA-based protected vinylboronate (1a) with R$^{2a}$-substituted diazomethane (1b) under the influence of metal catalysis, as illustrated in the following reaction scheme. Suitable methods to form the cyclopropylboronic acid are found in Tetrahedron Letters 51 (2010) 1009-1011, which is hereby incorporated by reference in its entirety.

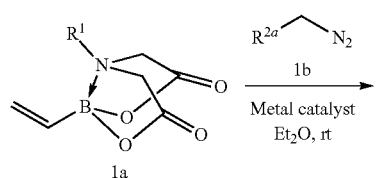

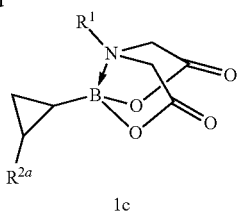

In the above scheme, R$^1$ and R$^{2a}$ are previously defined.

R$^{2a}$-Substituted diazomethane can be synthesized using standard procedures to prepare diazo compounds and are usually prepared immediately before their use. A suitable procedure to prepare a diazo compound is reaction of a nitrite ion with an amino compound to form an N-nitroso group and then an elimination reaction of the N-nitroso group to form a diazo compound. By way of example, when R$^1$ is optically active, for example, homochiral, the transformation of 1a to 1c can proceed in diastereoselective fashion.

Metal catalysis can aid the cyclopropanation reaction. In certain embodiments, the metal catalysis uses a metal catalyst such as, but not limited to, palladium, ruthenium, cobalt, copper, iron, osmium, rhenium, or rhodium. In certain embodiments, the metal catalysis uses palladium. In certain embodiments, the metal catalysis uses palladium acetate.

In certain embodiments, referring the scheme below, a boronate ester (2c) can be formed, for example, by cyclopropanation of dialkyl vinylboronate (2a) with (2,2,2-trifluoromethyl)diazomethane (2b) under the influence of palladium (II) catalysis, such as, but not limited to, palladium (II) acetate.

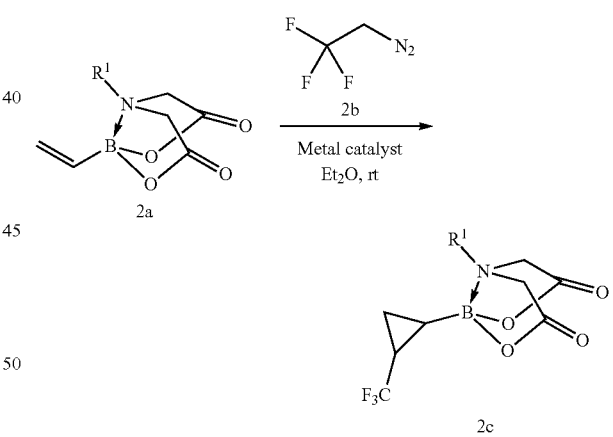

Substitution on the cyclopropyl ring on Compounds 1c and 2c can be achieved with further reactions as known to a skilled artisan. Substitution on the cyclopropyl ring can also be achieved with appropriate substitution of reactant Compound 1b.

Alternate Synthesis of Protected Cyclopropylboronic Acids

Protected cyclopropylboronic acids according to formula (3c) can be prepared by reaction of an appropriate imino-dicarboxylic acid with the corresponding unprotected cyclopropylboronic acid (3a), as illustrated in the following reaction scheme:

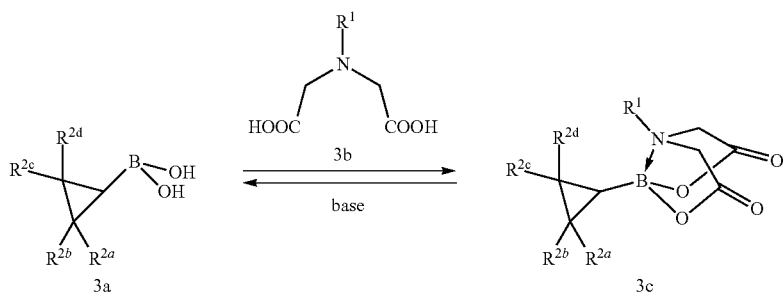

In a specific example, protected cyclopropylboronic acids according to formula (4c) can be prepared by reaction of pinene-derived iminodiacetic acid (PIDA) (4b) with the corresponding unprotected cyclopropylboronic acid (4a), as illustrated in the following reaction scheme:

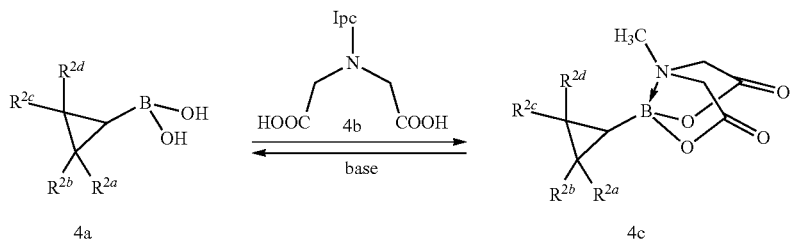

As used herein, "Ipc" represents an isopinocampheyl group. Protected cyclopropylboronic acids according to formula (5c) can be prepared by reaction of an appropriate PIDA-based group with the corresponding unprotected cyclopropylboronic acid (5a), as illustrated in the following reaction scheme:

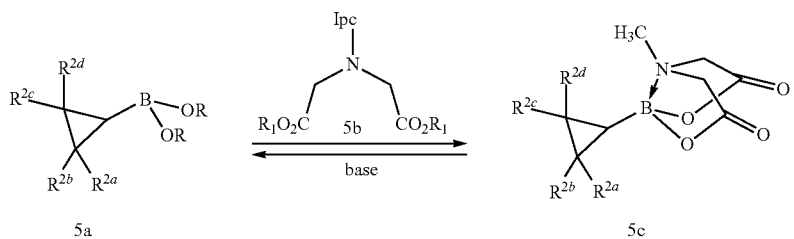

In the above scheme, R is an alkyl, such as methyl, n-propyl, isopropyl, n-butyl, or cyclized to form pinacolato boronate ester; $R^1$ is H, Li, Na, or K; and $R^{2a}$, $R^{2b}$, $R^{2c}$, and $R^{2d}$ are as defined herein. In certain embodiments in the reaction scheme above, the conditions can include heating in polar aprotic solvent, such as, but not limited to DMSO or DMF. In certain embodiments, in the reaction scheme above, $R^1$ is Na.

The protected cyclopropylboronic acid can be formed by condensation under Dean-Stark conditions. For instance, removal of water under Dean-Stark conditions can be condensation with heating of the reaction mixture up to at least about 35-45° C. In certain instances, heating of the reaction mixture is up to at least about 40° C. The conditions can also include the use of a co-solvent, such as DMSO, to partially dissolve the PIDA or PIDA-based ligand. The removal of water can also be performed by a variety of techniques, including, but not limited to, molecular sieves, azeotropic drying with acetonitrile, and the like.

In each case, the protected cyclopropylboronic acid can be deprotected by contact with a mild base, to provide the free cyclopropylboronic acid.

Synthesis of Precursor Cyclopropylboronic Acids

Suitable methods to form the compounds 3a, 4a, or 5a above are found in Tetrahedron Letters 51 (2010) 1009-1011, which is hereby incorporated by reference in its entirety. Referring to the scheme, the cyclopropylboronate ester (6c) can be formed, for example, by cyclopropanation of dialkyl vinylboronate (6a) with $R^{2a}$-substituted diazomethane (6b) under the influence of metal catalysis.

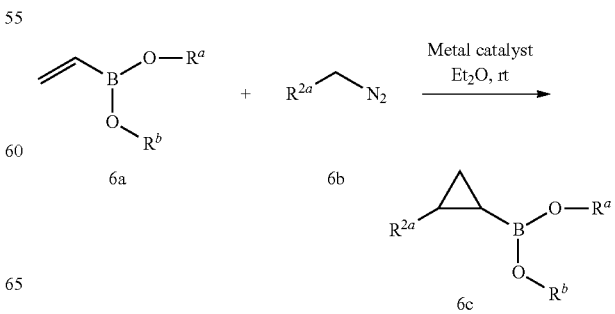

In the above scheme, $R^a$ and $R^b$ are organic groups as defined herein and $R^{2a}$ is as previously defined. In certain instances, $R^a$ and $R^b$ are alkyl groups, such as methyl, ethyl, propyl, or butyl.

Metal catalysis can aid the cyclopropanation reaction. In certain embodiments, the metal catalysis uses a metal catalyst such as, but not limited to, palladium, ruthenium, cobalt, copper, iron, osmium, rhenium, or rhodium. In certain embodiments, the metal catalysis uses palladium. In certain embodiments, the metal catalysis uses palladium acetate.

In certain embodiments, referring the scheme below, a boronate ester (7c) can be formed, for example, by cyclopropanation of dialkyl vinylboronate (7a) with (2,2,2-trifluoromethyl)diazomethane (7b) under the influence of palladium (II) catalysis, such as, but not limited to, palladium (II) acetate.

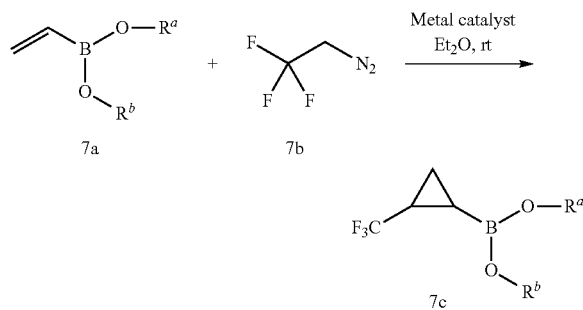

In the above schemes concerning cyclopropyl boronic acids (1a) and (2a), cyclopropylboronate esters (6c) and (7c) can be hydrolyzed to form cyclopropyl boronic acids (3a) and (4a). Hydrolysis of boronate esters can be accomplished in certain systems with thionyl chloride and pyridine.

Alternative Synthesis of Protected Cyclopropylboronic Acids

Protected cyclopropylboronic acids also can be formed without forming the free cyclopropylboronic acid. For example, a boronic halide (8a) can be reacted with a diacid or its corresponding salt to provide protected organoboronic acid (8c), as illustrated in the following reaction scheme:

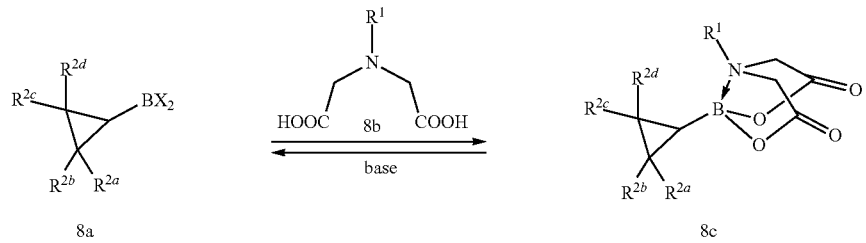

The boronic halide can be formed by treatment of a silane such as (cyclopropyl)-$SiR_3$ with $BBr_3$. (Qin, Y., *J. Am. Chem. Soc.*, 2002, 124, 12672-12673 and Qin, Y, *Macromolecules*, 2004, 37, 7123-7131.)

In certain embodiments, protected cyclopropylboronic acids including a PIDA boronate ester protecting group are readily purified by column chromatography. In some cases, this may be unusual for organoboronic acids, which are typically unstable to chromatographic techniques. These protected cyclopropylboronic acids also may be crystalline, which can facilitate purification, utilization, and storage. These protected cyclopropylboronic acids may also be stable to long term storage, including storage on the bench top under air. In some cases, this also may be unusual, as many organoboronic acids are unstable to long term storage.

Although many of the synthetic schemes discussed above do not illustrate the use of protecting groups, skilled artisans will recognize that in some instances certain substituents may include functional groups requiring protection. The exact identity of the protecting group used will depend upon, among other things, the identity of the functional group being protected and the reaction conditions used in the particular synthetic scheme, and will be apparent to those of skill in the art. Guidance for selecting protecting groups, their attachment and removal suitable for a particular application can be found, for example, in T. W. Greene and P. G. M. Wuts, "Protective Groups in Organic Synthesis", Fourth edition, Wiley, New York 2006.

Reactions Using Protected Cyclopropylboronic Acids

As will be readily appreciated by those of skill in the art, the presently disclosed organoboronic acids are useful in a variety of transition metal-catalyzed coupling reactions. Examples of such transition metal-catalyzed coupling reactions include those catalyzed by palladium, ruthenium, rhenium, rhodium, and the like. Examples of palladium-catalyzed coupling reactions for use with the present organoboronic acids include Suzuki reactions with aryl, heteroaryl and aliphatic coupling partners. Similarly, the present organoboronic acids are useful in rhodium catalyzed reactions, such as addition to sulfinyl imine substrates (see, Brak and Ellman, *J. Org. Chem.* 2010, 75, 3147-3150, which is incorporated herein by reference).

According to the embodiments, a Suzuki reaction can be carried out by coupling of a compound of Formulae I-IV with an organohalide or organo-pseudohalide in the presence of a palladium catalyst and a base, in an appropriate solvent to produce a cross-coupled product.

The protected cyclopropylboronic acid can undergo deprotection under mild conditions with high yields. Such a system can control the reactivity of boronic acids and expand the versatility of the Suzuki reaction or of other reactions of boronic acids. Thus, the protected cyclopropylboronic acid can deliver a substituted cyclopropyl group in a coupling reaction with improved selectivity compared to a corresponding reaction without use of the protected cyclopropylboronic acid.

In certain embodiments, reaction of the protected cyclopropylboronic acid with an organohalide or organo-pseudohalide can deliver a substituted cyclopropyl group to an organic group and displace a halogen or pseudohalogen group from the organohalide or organo-pseudohalide. In the scheme below, a protected cyclopropylboronic acid is coupled with an organohalide or organo-pseudohalide, $R^{10}$—Y, where $R^{10}$ is an organic group and Y is a halogen or pseudohalogen.

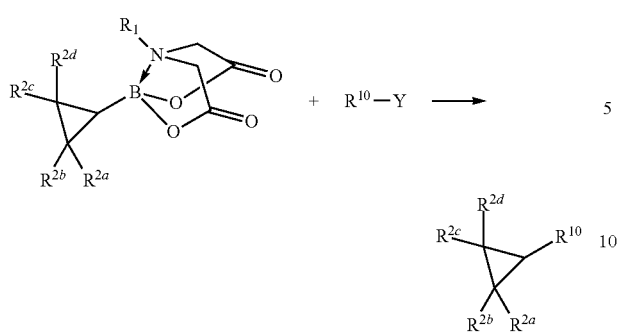

The embodiments provide a method of performing a chemical reaction, where the method includes:
contacting a protected organoboronic acid of formula I:

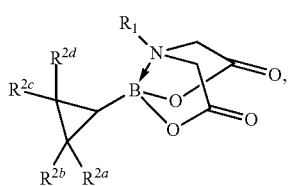

(I)

wherein
R$^1$ is selected from cycloalkyl and substituted cycloalkyl; and
R$^{2a}$, R$^{2b}$, R$^{2c}$, and R$^{2d}$ are independently selected from hydrogen, alkyl, substituted alkyl, halogen, hydroxyl, cyano, phosphate, alkoxy, substituted alkoxy, carboxyl, carboxyl ester, aryl, substituted aryl, heteroaryl, substituted heteroaryl, heterocyclyl, substituted heterocyclyl, alkenyl, substituted alkenyl, amino, substituted amino, acyl, acylamino, aminoacyl, alkoxycarbonylamino, thiol, alkylthiol, substituted thioalkoxy, and sulfonyl, wherein at least one of R$^{2a}$, R$^{2b}$, R$^{2c}$, and R$^{2d}$ is not hydrogen;

with an organohalide or organo-pseudohalide and a metal catalyst, in the presence of a base to provide a cross-coupled product.

The embodiments provide a method of performing a chemical reaction, where the method includes:
contacting a protected organoboronic acid of formula II:

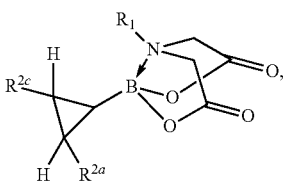

(II)

wherein
R$^1$ is selected from cycloalkyl and substituted cycloalkyl; and
R$^{2a}$ and R$^{2c}$ are independently selected from alkyl, substituted alkyl, halogen, hydroxyl, cyano, phosphate, alkoxy, substituted alkoxy, carboxyl, carboxyl ester, aryl, substituted aryl, heteroaryl, substituted heteroaryl, heterocyclyl, substituted heterocyclyl, alkenyl, substituted alkenyl, amino, substituted amino, acyl, acylamino, aminoacyl, alkoxycarbonylamino, thiol, alkylthiol, substituted thioalkoxy, and sulfonyl.

with an organohalide or organo pseudohalide and a metal catalyst, in the presence of a base to provide a cross-coupled product.

The embodiments provide a method of performing a chemical reaction, where the method includes:
contacting a protected organoboronic acid of formula III:

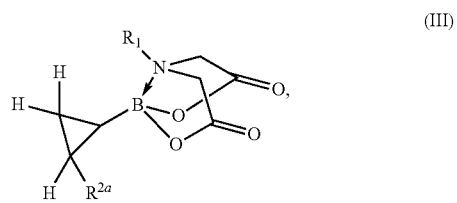

(III)

wherein
R$^1$ is selected from cycloalkyl and substituted cycloalkyl; and
R$^{2a}$ is selected from alkyl, substituted alkyl, halogen, hydroxyl, cyano, phosphate, alkoxy, substituted alkoxy, carboxyl, carboxyl ester, aryl, substituted aryl, heteroaryl, substituted heteroaryl, heterocyclyl, substituted heterocyclyl, alkenyl, substituted alkenyl, amino, substituted amino, acyl, acylamino, aminoacyl, alkoxycarbonylamino, thiol, alkylthiol, substituted thioalkoxy, and sulfonyl;

with an organohalide or organo pseudohalide and a metal catalyst, in the presence of a base to provide a cross-coupled product.

The embodiments provide a method of performing a chemical reaction, where the method includes:
contacting a protected organoboronic acid of formula IV:

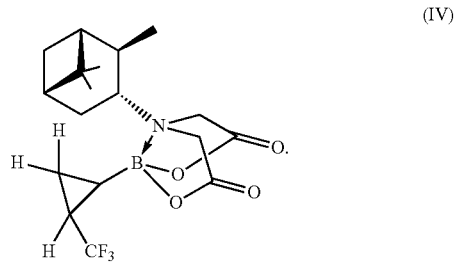 [SMILES: C[C@@H]1[C@H]2C[C@@H](C[C@H]1[N+]13CC(=O)O[B-]1(C1CC1C(F)(F)F)OC(=O)C3)C2(C)C]

(IV)

with an organohalide or organo pseudohalide and a metal catalyst, in the presence of a base to provide a cross-coupled product.

Substrates

The compound with which the protected cyclopropylboronic acid is reacted can be an organohalide or an organo-pseudohalide. An organohalide is an organic group having a halogen substituent. An organo-pseudohalide is an organic group having a pseudohalogen substituent.

An "organic group" or "organic compound" refers a group or compound that includes at least one carbon atom, but which may include additional substituent or functional groups, such as amino, alkoxy, cyano, hydroxy, carboxy, halo, acyl, oxo, hydrazino, alkyl, cycloalkyl, hetaryl, aryl, allylic, vinylic, arylene, benzylic, carboxyl, carboxyl ester, derivatives thereof, and the like. Organic groups and organic compounds can be cyclic or acyclic. Although an organic group or organic compound utilized herein can have essentially any number of carbon atoms, organic groups or organic compounds typically include about 2-20 carbon atoms, and more typically include about 3-15 carbon atoms. In certain embodiments, aryl, heteroaryl or aliphatic coupling partners are used.

A halogen or halide refers to —F, —Cl, —Br or —I. A pseudohalogen or pseudohalide refers to a polyatomic anion that resembles a halide ion in its acid-base, substitution, and redox chemistry, generally has low basicity, and forms a free radical under atom transfer radical polymerization conditions.

The substrate compound can be an organohalide, which is an organic compound that includes at least one halogen group. Examples of halogen groups that can be present in an organohalide compound include —F, —Cl, —Br or —I. The compound can be an organo-pseudohalide, which is an organic compound that includes at least one pseudohalogen group. Examples of pseudohalogen groups that can be present in an organo-pseudohalide compound include triflate (—O—S(=O)$_2$—CF$_3$), methanesulfonate (—O—S(=O)$_2$—CH$_3$), cyanate (—C≡N), azide (—N$_3$), thiocyanate (—N=C=S), thioether (—S—R), anhydride (—C(=O)—O—C(=O)—R), phenyl selenide (—Se—C$_6$H$_5$), alkoxy (—OR, e.g., OMe), diazo (—N$_2$), tosylate (—OTs), nonaflate (—ONf), and phosphonate (—OP(O)(OR)$_2$)

The halogen or pseudo-halogen group may be bonded to a carbon atom of a compound.

In certain embodiments, a substrate compound is of the formula:

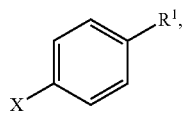

where X is a halide or pseudohalide and R$^1$ is carboxyl, carboxyl ester, or acyl.

In certain embodiments, a substrate compound is of the formula:

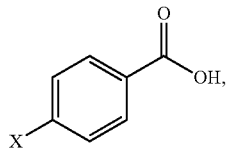

where X is a halide or pseudohalide.

In certain embodiments, a substrate compound is of the formula:

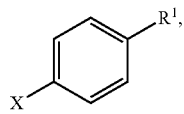

where X is a halide or pseudohalide and R$^1$ is carboxyl ester.

In certain embodiments, a substrate compound is of the formula:

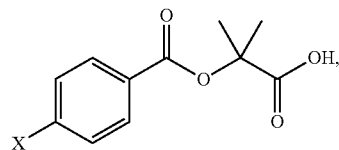

where X is a halide or pseudohalide.

In certain embodiments, a substrate compound is of the formula:

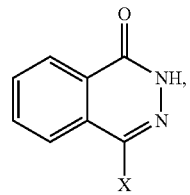

where X is a halide or pseudohalide.

In certain embodiments, a substrate compound is of the formula:

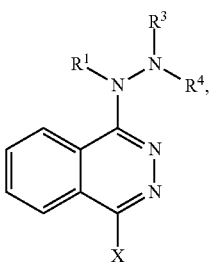

where X is a halide or pseudohalide; and R$^1$, R$^2$, R$^3$, and R$^4$ are each independently hydrogen, alkyl, aryl, heteroaryl, or acyl.

Palladium Catalyst

Typically, the Suzuki reaction can be carried out in the presence of a palladium catalyst. Examples of palladium catalysts and catalyst precursors include, but are not limited to palladium(II) acetate, palladium on activated charcoal, tetrakis(triphenylphosphine)palladium (0), and dichloro[1,1'-bis(diphenylphosphino)ferrocene]palladium(II).

In certain embodiments, the catalyst is formed in situ from palladium(II) acetate or palladium on activated charcoal. Palladium(II) acetate can be used in combination with a 2-(dicyclohexylphosphino)biphenyl type ligand (J. P. Wolfe et al., J. Am. Chem. Soc., 1999, 121, 9550-9561, which is hereby incorporated by reference in its entirety). The catalyst or catalyst precursor can also be encapsulated, such as for example the Pd EnCat™ type catalysts.

In certain embodiments, the reaction can employ a ligand selected from: a trialkyl phosphine, a triarylphosphine, or a combination thereof. For example, suitable ligands may include, but are not limited to, triphenylphosphine, tri-o-tolylphosphine, tri-m-tolylphosphine, tri-p-tolylphosphine, tricyclohexylphosphine, tri-t-butylphosphine, or a combination thereof. For an example of a method for using tricyclohexylphosphine see, Tetrahedron Letters 2002, 43, 6987-6890. The ligand can be added as a part of a metal complex, such as a palladium-ligand complex, may be added separately from a metal catalyst or catalyst precursor, or both.

Base

The base used to deprotect the PIDA cyclopropylboronate and promote the cross-coupling reaction can be a mild base. Deprotection of PIDA cyclopropylboronates with a mild base can provide a slower release of the unprotected cyclopropylboronic acid into the reaction mixture than that provided through deprotection with a strong base. This slower release can allow cross-coupling to occur between an organohalide or an organo-pseudohalide and a cyclopropylboronic acid that may otherwise degrade during the reaction. This slower release also can allow cross-coupling to occur with cyclopropylboronic acids that cannot be prepared or isolated in pure form.

In certain embodiments, the base is an anion selected from $[PO_4]^{3-}$, $[C_6H_5O]^-$, $[CO_3]^{2-}$ and $[HCO_3]^{1-}$, such as alkali and alkaline earth salts of these anions. Certain examples of such bases include, but are not limited to, $Li_3PO_4$, $Na_3PO_4$, $K_3PO_4$, $Li^+$ $[C_6H_5O]—$, $Na^+$ $[C_6H_5O]—$, $K^+$ $[C_6H_5O]—$, $Li_2CO_3$, $Na_2CO_3$, $K_2CO_3$, $MgCO_3$, $CaCO_3$, $LiHCO_3$, $NaHCO_3$, $KHCO_3$, and $Cs_2CO_3$.

In a Suzuki reaction, the reaction can include contacting the protected cyclopropylboronic acid and the organohalide or organo-pseudohalide with a palladium catalyst in the presence of a mild base. The protecting group can be removed from the boron atom in situ, providing a corresponding unprotected cyclopropylboronic acid, which can then cross-couple with the organohalide or organo-pseudohalide. In certain embodiments, the removal of the protecting group, such as a PIDA group or PIDA-based group, and the contacting of the resulting organoboronic acid and an organohalide or organo pseudohalide with a metal catalyst are performed simultaneously in the presence of a base. In certain embodiments, the removal of the protecting group, such as a PIDA group or a PIDA-based group, is performed prior to the contacting of the organoboronic acid and an organohalide or organo pseudohalide with a metal catalyst.

Solvent

The Suzuki reaction is typically run in an aprotic polar solvent or a protic polar solvent. For example, suitable aprotic polar solvents include, but are not limited to, acetonitrile, N,N-dimethylformamide, dimethoxyethane, tetrahydrofuran, dioxane, toluene, and xylene. In certain embodiments, the aprotic polar solvent is acetonitsrile, N,N-dimethylformamide, dimethoxyethane, or tetrahydrofuran. Suitable protic polar solvent include, but are not limited to, methanol, ethanol, butanol, n-propanol, isopropanol or a mixture of these solvents with water. In certain embodiments, the protic polar solvent is n-propanol, isopropanol or a mixture of these solvents with water.

Suzuki Reaction Conditions

The Suzuki reaction may be carried out under an inert atmosphere, for example under an argon or nitrogen atmosphere.

Forming a cross-coupled product in the reaction mixture can include maintaining the reaction mixture at a temperature and for a time sufficient to form a cross-coupled product. For example, forming a cross-coupled product in the reaction mixture can include maintaining the reaction mixture at a temperature from about 0 to 200° C. In certain embodiments, the forming includes maintaining the reaction mixture at a temperature from about 25 to 150° C. or from about 50 to 120° C. Forming a cross-coupled product in the reaction mixture can include maintaining the reaction mixture for a period of about 1 hour to 100 hours. In certain embodiments, the forming includes maintaining the reaction mixture for a period of about 2 hours to 72 hours or about 4 hours to 48 hours. In certain embodiments, the forming a cross-coupled product in the reaction mixture includes maintaining the reaction mixture at a temperature from about 25 to 150° C. for a period of about 2 hours to 72 hours, or maintaining the reaction mixture at a temperature from about 50 to 120° C. for a period of from about 4 hours to 48 hours. In some cases, microwave heating can be used to promote the reactions described herein.

One skilled in the art will be able to modify these conditions, in particular by applying the variants of the Suzuki reaction which are described in the literature (N. Miyaura & A. Suzuki, Chem. Rev., 1995, 95, 2457-2483; A. Suzuki, J. Organomet. Chem., 1999, 576, 147-168, which is hereby incorporated by reference in its entirety).

Stereochemistry of Products

In certain embodiments, the method facilitates directly obtaining a product compound with a high yield and favoring a certain stereochemistry.

In certain embodiments, the Suzuki reaction uses a protected organoboronic acid of the formula III-IV with a trans stereochemistry with respect to the cyclopropyl ring. In some cases, the favored product compound from the reaction includes a trans stereochemistry with respect to the substituents on the cyclopropyl ring. For example, the scheme below shows a general reaction which uses a trans stereoisomer of a protected organoboronic acid of the formula III-IV, resulting in a favored product compound that includes a trans stereochemistry with respect to the substituents on the cyclopropyl ring.

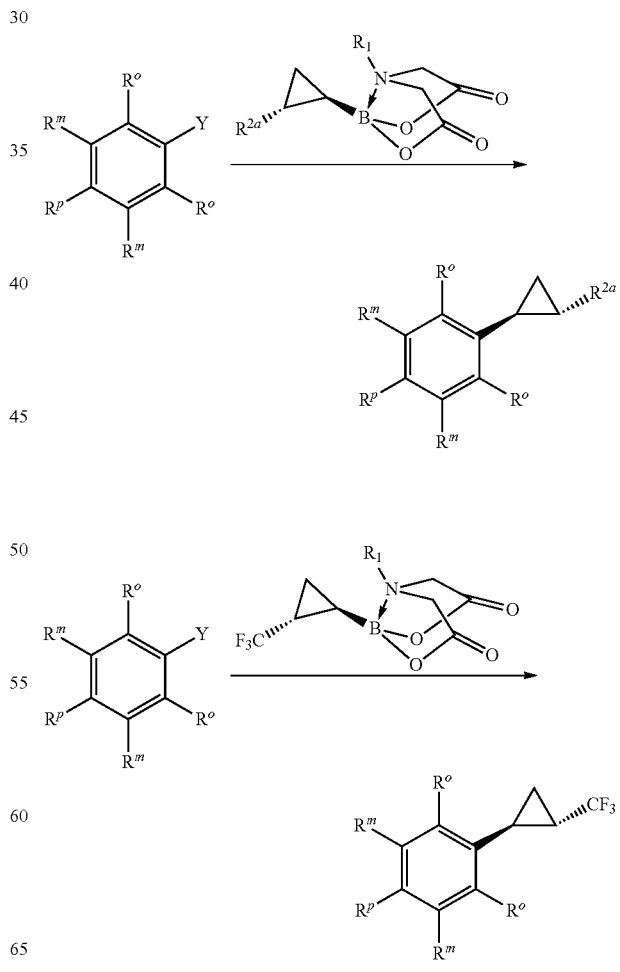

In certain embodiments, with use of a protected organoboronic acid of the formula III-IV with a trans stereochemistry with respect to the cyclopropyl ring, the stereochemistry ratio (trans:cis) of the product is about 100 to 0; 99 to 1; 98 to 2; 97 to 3; 96 to 4; 95 to 5; 94 to 6; 93 to 7; 92 to 8; 91 to 9; 90 to 10; 85 to 15; 80 to 20; 75 to 25; 70 to 30; 65 to 45; 60 to 40; or 55 to 45.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used.

Example 1

Preparation of trans-2-(trifluoromethyl)cyclopropylboronic acid PIDA ester

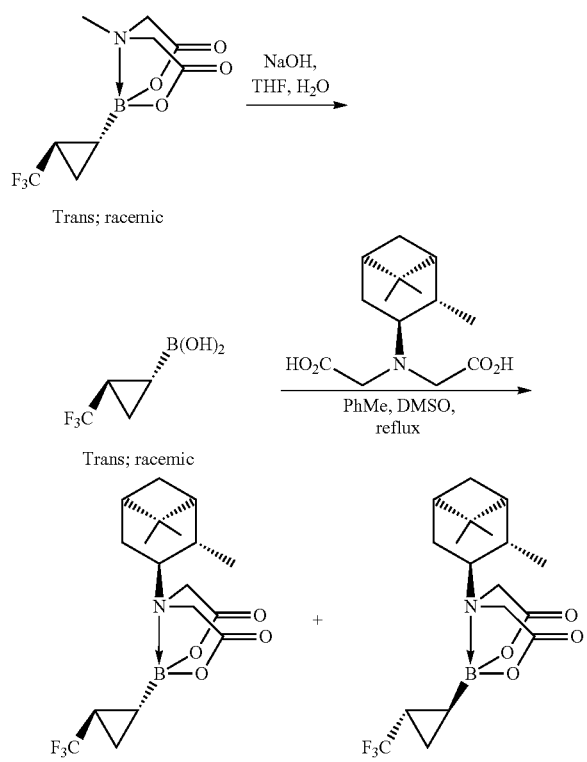

Step 1: Hydrolysis of MIDA ester

Sodium hydroxide 1M in H$_2$O (3 mL, 3.0 mmol) was added in one portion to a stirred solution of trans-2-(trifluoromethyl)cyclopropylboronic acid MIDA ester (265 mg, 1.0 mmol; prepared according to WO2012075316) in THF (10 mL) at room temperature. The mixture was stirred vigorously for 20 min. Saturated NH$_4$Cl in H$_2$O (10 mL) was added to quench the reaction and the mixture stirred for a further 5 min, then transferred to a separating funnel with the aid of Et$_2$O (10 mL). The aqueous and organic layers were partitioned and the organic layer was washed with saturated NH$_4$Cl in H$_2$O (10 mL). The combined aqueous layers were extracted with 1:1 THF/Et$_2$O (15 mL total). The combined organic layers were dried (Na$_2$SO$_4$), filtered and the solvent removed under vacuum to leave a crude solid that was used directly in the next step.

Reference for the procedure is made to *J. Am. Chem. Soc.* 2011, 133, 13774-13777 and the accompanying Supporting Information (S12), each of which is hereby incorporated by reference in its entirety.

Step 2: Formation of PIDA Ester

The solid from the above step was suspended in toluene (15 mL) and DMSO (0.5 mL) and 2,2'-((1S,2S,3S,5R)-2,6,6-trimethylbicyclo[3.1.1]heptan-3-ylazanediyl)diacetic acid (404 mg, 1.5 mmol; Aldrich catalogue number PIDA025) was added. The mixture was then heated to reflux with a Dean-Stark apparatus. When at reflux, heating was continued for an additional 2 hours. After allowing the mixture to cool, silica gel (2 g) was added and the mixture was concentrated under vacuum. The product was dry-loaded onto silica gel and was purified by column chromatography on silica gel (ISCO 40 g Gold column was used for the purification) using hexanes/EtOAc (1:0 to 1:1) as eluent to give pure diastereomer A (108 mg, 56% theoretical yield; absolute stereochemistry not established) as a solid, followed by pure diastereomer B (102 mg, 53% theoretical yield; absolute stereochemistry not established) as an oil that crystallized on standing.

KMnO$_4$ solution was used to visualize the products on TLC.

The above reaction may also be performed on a larger-scale, for instance, using 5 mmol of MIDA ester starting material and scaling the other reagents as appropriate.

Both diastereomer A and diastereomer B may include excess 2,2'-((1S,2S,3S,5R)-2,6,6-trimethylbicyclo[3.1.1]heptan-3-ylazanediyl)diacetic acid, which also elutes from the column. Excess 2,2'-((1S,2S,3S,5R)-2,6,6-trimethylbicyclo[3.1.1]heptan-3-ylazanediyl)diacetic acid may be removed by washing with NaHCO$_3$ solution.

Data for Diastereomer A:

$^1$H NMR (Acetone-d$_6$, 300 MHz): δ 4.39-4.01 (m, 4H), 2.75-2.64 (m, 1H), 2.59-2.42 (m, 2H), 2.08-2.03 (m, 1H), 1.98-1.93 (m, 1H), 1.81-1.62 (m, 2H), 1.41 (d, J=6.9 Hz, 3H), 1.28 (s, 3H), 1.22-1.05 (m, 2H), 1.03 (s, 3H), 1.00-0.94 (m, 1H), 0.83-0.76 (m, 1H), 0.51-0.43 (m, 1H)

$^{13}$C NMR (Acetone-d$_6$, 75 MHz): δ 171.0, 168.1, 127.2 (q, J=268 Hz), 69.6, 62.5, 56.7, 50.8, 42.4, 40.4, 40.0, 32.8, 32.1, 28.2, 24.5, 24.0, 17.3 (q, J=36 Hz), 6.7 (q, J=2.7 Hz), 1.9

$^{19}$F NMR (Acetone-d$_6$, 282 MHz): −66.9 (d, J=6.8 Hz)

Data for Diastereomer B:

$^1$H NMR (Acetone-d$_6$, 300 MHz): δ 4.36-4.00 (m, 4H), 2.84-2.73 (m, 1H), 2.57-2.40 (m, 2H), 2.09-2.03 (m, 1H), 1.98-1.93 (m, 1H), 1.77-1.69 (m, 1H), 1.67-1.57 (m, 1H), 1.38 (d, J=6.9 Hz, 3H), 1.28 (s, 3H), 1.22-1.08 (m, 2H), 1.05 (s, 3H), 1.03-0.95 (m, 1H), 0.77-0.71 (m, 1H), 0.56-0.48 (m, 1H)

$^{13}$C NMR (Acetone-d$_6$, 75 MHz): δ 171.0, 168.2, 127.2 (q, J=268 Hz), 69.4, 62.3, 56.6, 50.9, 42.3, 40.4, 40.0, 33.0, 31.9, 28.2, 24.4 (x2), 18.3 (q, J=36 Hz), 5.9 (q, J=2.7 Hz), 1.7

$^{19}$F NMR (Acetone-d$_6$, 282 MHz): −67.1 (d, J=7.1 Hz)

Example 2

Use of trans-2-(trifluoromethyl)cyclopropylboronic acid PIDA ester in Suzuki Reactions

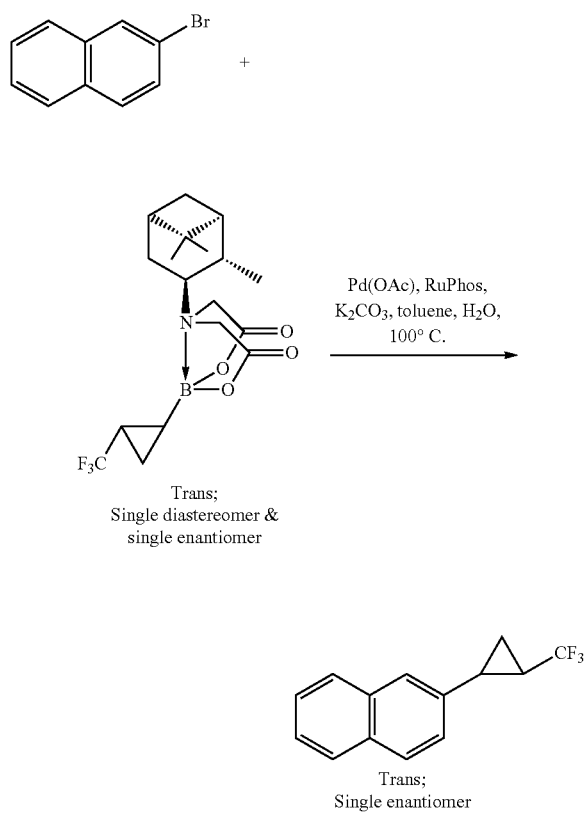

A mixture of trans-2-(trifluoromethyl)cyclopropylboronic acid PIDA ester diastereomer B (100 mg, 0.26 mmol), 2-bromonaphthylene (36 mg, 0.17 mmol), palladium(II) acetate (3.9 mg, 0.017 mmol), RuPhos (16.2 mg, 0.035 mmol) and $K_2CO_3$ (96 mg, 0.7 mmol) in toluene (2.5 mL) and $H_2O$ (0.5 mL) was de-gassed with nitrogen for 5 min then placed under an atmosphere of nitrogen and heated to 100° C. The mixture was stirred at 100° C. and stirred for about 6 hr. After allowing the mixture to cool, the mixture was diluted with EtOAc (15 mL) and $H_2O$ (10 mL) and the mixture was filtered through Celite. The filter cake was washed with EtOAc (2×10 mL). The filtrate was partitioned and the aqueous layer was extracted with EtOAc (1×10 mL). The combined organic layers were dried ($Na_2SO_4$), filtered and the solvent removed under vacuum to leave a crude residue. The residue was dry-loaded onto silica gel (1 g) and then purified by column chromatography on silica gel (ISCO 12 g silica column) using Hexanes/EtOAc (1:0 to 9:1) as eluent to give the product (34 mg, 83%) as a solid.

Analysis by chiral HPLC indicated the above product was chirally-pure in the range 80:20, 90:10, 95:5, 99:1.

Reference for the procedure is made to WO2012075316, which is hereby incorporated by reference in its entirety.

Example 3

Use of trans-2-(trifluoromethyl)cyclopropylboronic acid PIDA ester in Suzuki Reactions

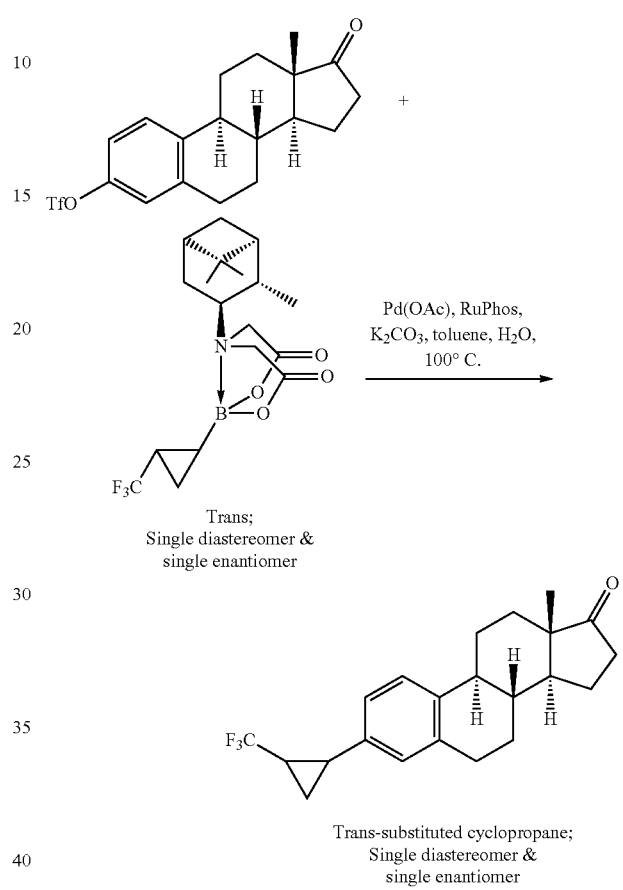

A mixture of trans-2-(trifluoromethyl)cyclopropylboronic acid PIDA ester diastereomer A (100 mg, 0.26 mmol), estrone triflate (69 mg, 0.17 mmol; for preparation see *J. Am. Chem. Soc.* 2010, 132, 12150-12154), palladium(II) acetate (3.9 mg, 0.017 mmol), RuPhos (16.2 mg, 0.035 mmol) and $K_2CO_3$ (96 mg, 0.7 mmol) in toluene (2.5 mL) and $H_2O$ (0.5 mL) was de-gassed with nitrogen for 5 min and then placed under an atmosphere of nitrogen and heated to 100° C. The mixture was stirred at 100° C. and stirred overnight. After allowing the mixture to cool, the mixture was diluted with EtOAc (15 mL) and $H_2O$ (10 mL) and the mixture was filtered through Celite. The filter cake was washed with EtOAc (2×10 mL). The filtrate was partitioned and the aqueous layer extracted with EtOAc (1×10 mL). The combined organic layers were dried ($Na_2SO_4$), filtered and the solvent removed under vacuum to leave a crude residue. The residue was dry-loaded onto silica gel (1 g) then purified by column chromatography on silica gel (ISCO 24 g silica column) using Hexanes/EtOAc (1:0 to 9:1) as eluent to give the product as a solid.

m/z=363.52 $[M+H]^+$ $^{19}F$ NMR ($CDCl_3$, 282 MHz): −66.7 (d, J=6.8 Hz)

Example 4

Preparation of trans-2-(trifluoromethyl)cyclopropylboronic acid PIDA ester

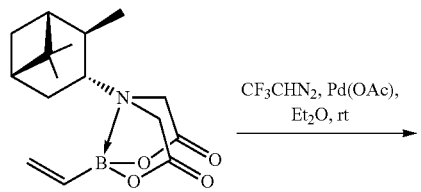

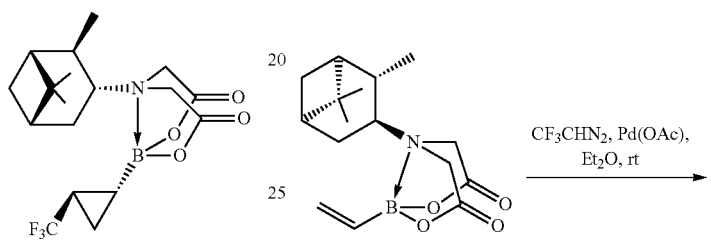

Step 1: Preparation of Trifluoromethyl Diazomethane

Sodium nitrite (4.6 g, 66 mmol) in water (10 mL) is added in one portion to a stirred solution of 2,2,2-trifluoroethylamine hydrochloride (8.1 g, 60 mmol) in water (25 mL) and ether (45 mL) at 0° C. The reaction vessel is sealed with a Teflon stopper and the mixture is stirred from 0° C. to room temperature and is stirred at room temperature for approximately 3 hours. The mixture is then partitioned in a separating funnel and the ether layer containing the product is used directly in the next step without further purification. The yield of the trifluoromethyl diazomethane product is assumed to be approximately 50% based on literature citation herein (=3.32 g).

A safety notice for the procedure: Diazo compounds are potentially explosive. The reaction is performed behind a blast shield in glassware free from cracks or prominent scratches and glassware is inspected prior to use.

Reference for the procedure is made to *J. Am. Chem. Soc.* 1943, 65, 1458, which is hereby incorporated by reference in its entirety.

Step 2: Preparation of trans-2-(trifluoromethyl)cyclopropylboronic Acid PIDA Ester A mixture of trifluoromethyl diazomethane (3.32 g, 30 mmol) in $Et_2O$ (45 mL) is added dropwise to a stirred suspension of vinylboronic acid PIDA ester (Sigma-Aldrich, St. Louis, Mo.; See also Li, J. & Burke, M. D., *J. Am. Chem. Soc.* 2011, 133, 13774-13777; 2.73 g, 9.0 mmol) and $Pd(OAc)_2$ (50 mg) in $Et_2O$ at room temperature. After adding for 10 minutes (about a quarter of the trifluoromethyl diazomethane has been added at this stage), more $Pd(OAc)_2$ (50 mg) and $Et_2O$ (100 mL) is added, and trifluoromethyl diazomethane is added dropwise for another 20 minutes (approximately three quarters is added after this time). EtOAc (50 mL) and $Pd(OAc)_2$ (50 mg) are added at this point and the remaining trifluoromethyl diazomethane is added dropwise over 10 minutes. After complete addition of the trifluoromethyl diazomethane the mixture is analysed by TLC which indicates the reaction is complete. The solvent is removed under vacuum and the residue is dry-loaded on to silica gel and purified by column chromatography on silica gel using EtOAc as eluent to give the product as a solid.

In certain embodiments, the ratio of diastereomers (trans:cis) is 50:50 or more, such as 60:40 or more, including 70:30 or more, or 80:20 or more, or 90:10 or more, or 95:5 or more.

Example 5

The reaction can also be performed with a PIDA reagent derived from (−)-alpha-pinene.

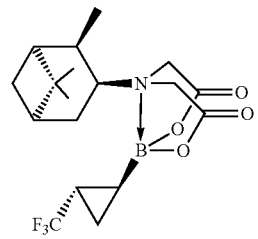

From the above PIDA reagents, the following boron species may also be produced:

For example, from diastereomer 1 (e.g., from Example 4 above):

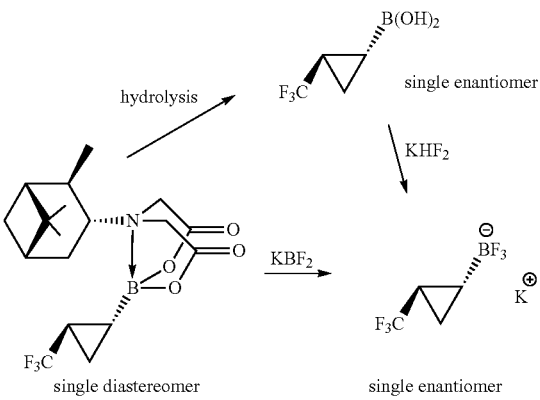

For example, from diastereomer 2 (e.g, from Example 5 above):

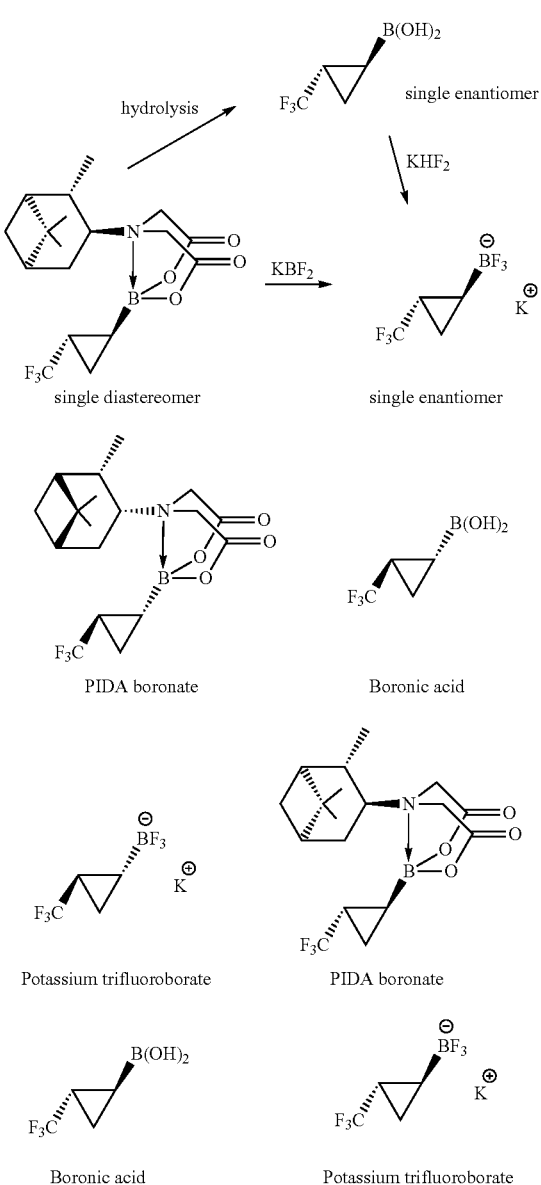

The boron species above find use in the following types of reaction: "slow-release" Suzuki coupling (PIDA reagent or trifluoroborate); Suzuki reactions (boronic acid); additions to sulfoxideimines (all species); Petasis Mannich reactions (all species); Barluenga boronic coupling (all species); Rh-catalyzed 1,4-additions to enones (all species); and the like.

For example, the boron species above find use in Suzuki couplings using the following organohalide or organo pseudohalide reagents (see, e.g, WO2012075316):

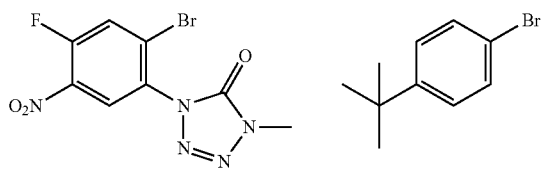

-continued

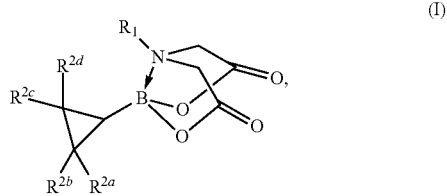

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A protected organoboronic acid of the formula I:

wherein
R$^1$ is selected from cycloalkyl and substituted cycloalkyl; and

R$^{2a}$, R$^{2b}$, R$^{2c}$, and R$^{2d}$ are independently selected from hydrogen, alkyl, substituted alkyl, halogen, hydroxyl, cyano, phosphate, alkoxy, substituted alkoxy, carboxyl, carboxyl ester, aryl, substituted aryl, heteroaryl, substituted heteroaryl, heterocyclyl, substituted heterocyclyl, alkenyl, substituted alkenyl, amino, substituted amino, acyl, acylamino, aminoacyl, alkoxycarbonylamino, thiol, alkylthiol, substituted thioalkoxy, and sulfonyl, wherein at least one of R$^{2a}$, R$^{2b}$, R$^{2c}$, and R$^{2d}$ is not hydrogen.

2. The protected organoboronic acid of claim 1, wherein R$^1$ is homochiral.

3. The protected organoboronic acid of claim 1, wherein R$^1$ is substituted cycloalkyl.

4. The protected organoboronic acid of claim 1, wherein R$^1$ is isopinocampheyl.

5. The protected organoboronic acid of claim 1, wherein one of R$^{2a}$, R$^{2b}$, R$^{2c}$, and R$^{2d}$ is substituted alkyl and the others are hydrogen.

6. The protected organoboronic acid of claim 1, wherein one of R$^{2a}$, R$^{2b}$, R$^{2c}$, and R$^{2d}$ is trifluoromethyl and the others are hydrogen.

7. The protected organoboronic acid of claim 1, wherein the protected organoboronic acid is of the formula II:

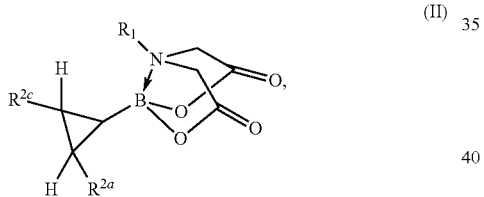

(II)

wherein
R$^1$ is selected from cycloalkyl and substituted cycloalkyl; and

R$^{2a}$ and R$^{2c}$ are independently selected from hydrogen, alkyl, substituted alkyl, halogen, hydroxyl, cyano, phosphate, alkoxy, substituted alkoxy, carboxyl, carboxyl ester, aryl, substituted aryl, heteroaryl, substituted heteroaryl, heterocyclyl, substituted heterocyclyl, alkenyl, substituted alkenyl, amino, substituted amino, acyl, acylamino, aminoacyl, alkoxycarbonylamino, thiol, alkylthiol, substituted thioalkoxy, and sulfonyl.

8. The protected organoboronic acid of claim 7, wherein R$^1$ is substituted cycloalkyl.

9. The protected organoboronic acid of claim 7, wherein R$^1$ is isopinocampheyl.

10. The protected organoboronic acid of claim 7, wherein one of R$^{2a}$ and R$^{2c}$ is substituted alkyl.

11. The protected organoboronic acid of claim 7, wherein one of R$^{2a}$ and R$^{2c}$ is trifluoromethyl.

12. The protected organoboronic acid of claim 1, wherein the protected organoboronic acid is of the formula III:

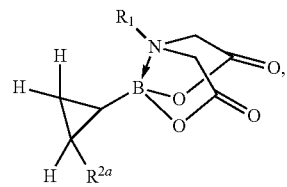

(III)

wherein
R$^1$ is selected from cycloalkyl and substituted cycloalkyl; and

R$^{2a}$ is selected from alkyl, substituted alkyl, halogen, hydroxyl, cyano, phosphate, alkoxy, substituted alkoxy, carboxyl, carboxyl ester, aryl, substituted aryl, heteroaryl, substituted heteroaryl, heterocyclyl, substituted heterocyclyl, alkenyl, substituted alkenyl, amino, substituted amino, acyl, acylamino, aminoacyl, alkoxycarbonylamino, thiol, alkylthiol, substituted thioalkoxy, and sulfonyl.

13. The protected organoboronic acid of claim 12, wherein R$^1$ is substituted cycloalkyl.

14. The protected organoboronic acid of claim 12, wherein R$^1$ is isopinocampheyl.

15. The protected organoboronic acid of claim 12, wherein R$^{2a}$ is substituted alkyl.

16. The protected organoboronic acid of claim 12, wherein R$^{2a}$ is trifluoromethyl.

17. The protected organoboronic acid of claim 12, wherein the protected organoboronic acid has a trans stereochemistry with respect to the cyclopropyl ring.

18. The protected organoboronic acid of claim 1, wherein the protected organoboronic acid is of the formula IV:

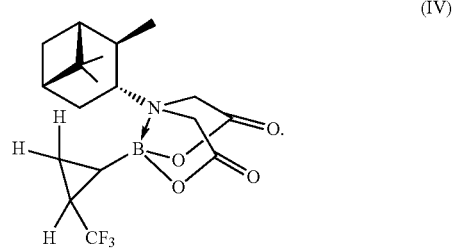

(IV)

19. The protected organoboronic acid of claim 18, wherein the protected organoboronic acid has a trans stereochemistry with respect to the cyclopropyl ring.

20. A method of performing a chemical reaction comprising:
contacting a protected organoboronic acid of formula I:

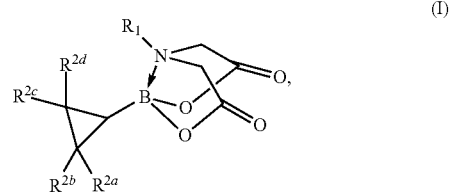

(I)

wherein
R$^1$ is selected from cycloalkyl and substituted cycloalkyl; and $R^{2a}$, $R^{2b}$, $R^{2c}$, and $R^{2d}$ are independently selected from hydrogen, alkyl, substituted alkyl, halogen, hydroxyl, cyano, phosphate, alkoxy, substituted alkoxy, carboxyl, carboxyl ester, aryl, substituted aryl, heteroaryl, substituted heteroaryl, heterocyclyl, substituted heterocyclyl, alkenyl, substituted alkenyl, amino, substituted amino, acyl, acylamino, aminoacyl, alkoxycarbonylamino, thiol, alkylthiol, substituted thioalkoxy, and sulfonyl, wherein at least one of $R^{2a}$, $R^{2b}$, $R^{2c}$, and $R^{2d}$ is not hydrogen;

with an organohalide or organo pseudohalide and a metal catalyst, in the presence of a base to provide a cross-coupled product.

21. The method of claim 20, wherein $R^1$ is substituted cycloalkyl.

22. The method of claim 20, wherein $R^1$ is isopinocampheyl.

23. The method of claim 20, wherein one of $R^{2a}$, $R^{2b}$, $R^{2c}$, and $R^{2d}$ is substituted alkyl and the others are hydrogen.

24. The method of claim 20, wherein one of $R^{2a}$, $R^{2b}$, $R^{2c}$, and $R^{2d}$ is trifluoromethyl and the others are hydrogen.

25. The method of claim 20, further comprising removing the PIDA group or PIDA-based group from the boron to form an organoboronic acid, and contacting the organoboronic acid and the organohalide or organo pseudohalide with the metal catalyst to provide the cross-coupled product.

26. The method of claim 25, wherein the removing the PIDA group or PIDA-based group and the contacting the organoboronic acid and the organohalide or organo pseudohalide with the metal catalyst are performed simultaneously in the presence of the base.

27. The method of claim 25, wherein the removing the PIDA group or PIDA-based group is performed prior to the contacting the organoboronic acid and the organohalide or organo pseudohalide with the metal catalyst.

28. The method of claim 20, wherein the protected organoboronic acid is of formula II:

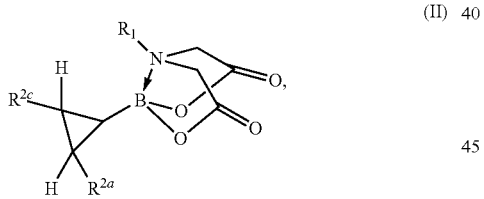

(II)

wherein
$R^1$ is selected from cycloalkyl and substituted cycloalkyl; and
$R^{2a}$ and $R^{2c}$ are independently selected from alkyl, substituted alkyl, halogen, hydroxyl, cyano, phosphate, alkoxy, substituted alkoxy, carboxyl, carboxyl ester, aryl, substituted aryl, heteroaryl, substituted heteroaryl, heterocyclyl, substituted heterocyclyl, alkenyl, substituted alkenyl, amino, substituted amino, acyl, acylamino, aminoacyl, alkoxycarbonylamino, thiol, alkylthiol, substituted thioalkoxy, and sulfonyl.

29. The method of claim 28, wherein $R^1$ is substituted cycloalkyl.

30. The method of claim 28, wherein $R^1$ is isopinocampheyl.

31. The method of claim 28, wherein one of $R^{2a}$ and $R^{2c}$ is substituted alkyl.

32. The method of claim 28, wherein one of $R^{2a}$ and $R^{2c}$ is trifluoromethyl.

33. The method of claim 28, further comprising removing the PIDA group or PIDA-based group from the boron to form an organoboronic acid, and contacting the organoboronic acid and the organohalide or organo pseudohalide with the metal catalyst to provide the cross-coupled product.

34. The method of claim 33, wherein the removing the PIDA group or PIDA-based group and the contacting the organoboronic acid and the organohalide or organo pseudohalide with the metal catalyst are performed simultaneously in the presence of the base.

35. The method of claim 33, wherein the removing the PIDA group or PIDA-based group is performed prior to the contacting the organoboronic acid and the organohalide or organo pseudohalide with the metal catalyst.

36. The method of claim 20, wherein the protected organoboronic acid is of formula III:

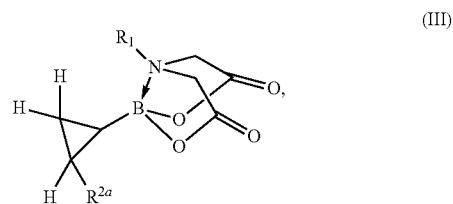

(III)

wherein
$R^1$ is selected from cycloalkyl and substituted cycloalkyl; and
$R^{2a}$ is selected from alkyl, substituted alkyl, halogen, hydroxyl, cyano, phosphate, alkoxy, substituted alkoxy, carboxyl, carboxyl ester, aryl, substituted aryl, heteroaryl, substituted heteroaryl, heterocyclyl, substituted heterocyclyl, alkenyl, substituted alkenyl, amino, substituted amino, acyl, acylamino, aminoacyl, alkoxycarbonylamino, thiol, alkylthiol, substituted thioalkoxy, and sulfonyl.

37. The method of claim 36, wherein $R^1$ is substituted cycloalkyl.

38. The method of claim 36, wherein $R^1$ is isopinocampheyl.

39. The method of claim 36, wherein $R^{2a}$ is substituted alkyl.

40. The method of claim 36, wherein $R^{2a}$ is trifluoromethyl.

41. The method of claim 36, further comprising removing the PIDA group or PIDA-based group from the boron to form an organoboronic acid, and contacting the organoboronic acid and the organohalide or organo pseudohalide with the metal catalyst, to provide the cross-coupled product.

42. The method of claim 41, wherein the removing the PIDA group or PIDA-based group and the contacting the organoboronic acid and the organohalide or organo pseudohalide with the metal catalyst are performed simultaneously in the presence of the base.

43. The method of claim 41, wherein the removing the PIDA group or PIDA-based group is performed prior to the contacting the organoboronic acid and the organohalide or organo pseudohalide with the metal catalyst.

44. The method of claim 20, wherein the protected organoboronic acid is of formula IV:

(IV)

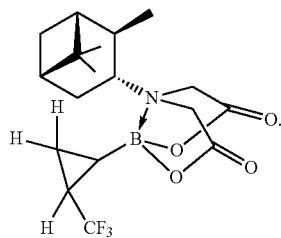

45. The method of claim 44, further comprising removing the PIDA group or PIDA-based group from the boron to form an organoboronic acid, and contacting the organoboronic acid and the organohalide or organo pseudohalide with the metal catalyst to provide the cross-coupled product.

46. The method of claim 44, wherein the removing the PIDA group or PIDA-based group and the contacting the organoboronic acid and the organohalide or organo pseudohalide with the metal catalyst are performed simultaneously in the presence of the base.

47. The method of claim 44, wherein the removing the PIDA group or PIDA-based group is performed prior to the contacting the organoboronic acid and the organohalide or organo pseudohalide with the metal catalyst.

48. The method of claim 20, wherein the metal catalyst is a palladium catalyst.

49. The method of claim 20, wherein the metal catalyst is palladium (II) acetate.

50. The method of claim 20, wherein the base is an anion selected from $[PO_4]^{3-}$, $[C_6H_5O]^-$, $[CO_3]^{2-}$ and $[HCO_3]^{1-}$.

51. A method of forming a compound of formula III (III)

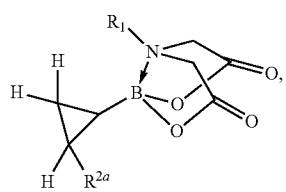

wherein
$R^1$ is selected from cycloalkyl and substituted cycloalkyl; and
$R^{2a}$ is selected from alkyl, substituted alkyl, halogen, hydroxyl, cyano, phosphate, alkoxy, substituted alkoxy, carboxyl, carboxyl ester, aryl, substituted aryl, heteroaryl, substituted heteroaryl, heterocyclyl, substituted heterocyclyl, alkenyl, substituted alkenyl, amino, substituted amino, acyl, acylamino, aminoacyl, alkoxycarbonylamino, thiol, alkylthiol, substituted thioalkoxy, and sulfonyl;
comprising reacting a compound of formula 1a:

(1a)

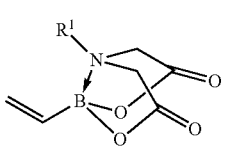

with a compound of formula 1b:

(1b)

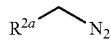

in the presence of a metal catalyst.

52. A method of forming a compound of formula IV (IV)

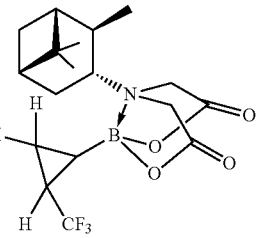

comprising reacting a compound of formula 2a:

(2a)

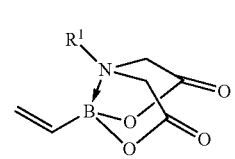

with a compound of formula 2b:

(2b)

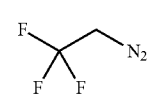

in the presence of a metal catalyst.

53. The method of claim 20, wherein the metal catalyst is selected from palladium, ruthenium, rhenium and rhodium.

54. The method of claim 20, wherein the metal catalyst is selected from palladium(II) acetate, palladium on activated charcoal, tetrakis(triphenylphosphine)palladium (0), and dichloro[1,1'-bis(diphenylphosphino)ferrocene]palladium (II).

55. The method of claim 51, wherein the metal catalyst is selected from palladium, ruthenium, cobalt, copper, iron, osmium, rhenium and rhodium.

56. The method of claim 52, wherein the metal catalyst is selected from palladium, ruthenium, cobalt, copper, iron, osmium, rhenium and rhodium.

* * * * *